US00PP17505P3

(12) United States Plant Patent

Lal et al.

(10) Patent No.: US PP17,505 P3

(45) Date of Patent: Mar. 20, 2007

(54) *PLANTAGO OVATA* PLANT NAMED 'MAYURI'

(50) Latin Name: *Plantago ovata*
Varietal Denomination: Mayuri

(75) Inventors: Raj Kishori Lal, Lucknow (IN); Nilakshi Singh, Lucknow (IN); Hari Om Misra, Lucknow (IN); Jawahar Ram Sharma, Lucknow (IN); Janak Raj Bahl, Lucknow (IN); Ajit Kumar Shasany, Lucknow (IN); Suman Preet Singh Khanuja, Lucknow (IN)

(73) Assignee: Council of Scientific Industrial Research, New Delhi (IN)

( * ) Notice: Subject to any disclaimer, the term of this patent is extended or adjusted under 35 U.S.C. 154(b) by 0 days.

(21) Appl. No.: 10/404,304

(22) Filed: Mar. 31, 2003

(65) Prior Publication Data

US 2004/0199969 P1 Oct. 7, 2004

(51) Int. Cl.
*A01H 5/00* (2006.01)

(52) U.S. Cl. ..... Plt./258

(58) Field of Classification Search ..... Plt./258
See application file for complete search history.

*Primary Examiner*—Anne Marie Grunberg
*Assistant Examiner*—June Hwu
(74) *Attorney, Agent, or Firm*—Merchant & Gould P.C,

(57) ABSTRACT

This invention relates to a new distinct early maturing, high seed and husk yielding variety of psyllium (*Plantago ovata*) designated as var. 'Mayuri' with the distinct pigment marker of the panicles relatable to the maturity thereby indicating the right harvesting stage to prevent the seed shattering, a problem in psyllium. This variety was developed by mutation breeding (gamma rays irradiation) and propagated by seeds for commercial cultivation. The new variety could be differentiated from the other variety through unique RAPD profile and has been tested for uniformity and stability of characters defined. Psyllium plant 'Mayuri' with stage marker and early maturity.

1 Drawing Sheet

FIELD OF INVENTION

Genus and species: *Plantago ovata.*

Variety denomination: Mayuri.

The present invention relates to a new distinct early maturing, high seed and husk yielding variety of the genus *Plantago,* species *ovata,* (common name "psyllium") designated as the variety 'Mayuri'.

This invention further relates to the distinct pigment indicator marker of the panicles relatable to the maturity, serving as signal for harvesting stage. The new distinct plant variety of psyllium has been developed by mutation breeding (gamma rays irradiation). The variety can be propagated asexually, but can conveniently be propagated by seed for commercial cultivation.

BACKGROUND OF THE INVENTION

Psyllium (*Plantago ovata*), family—Plantaginaceae a plant of west Asian origin was introduced into India the middle age. It is important for its seeds and husk in traditional system of medicine. India continues to hold a monopoly in its production and trade in the world market. Thus, isabgol/psyllium is a major foreign exchange earner. Owning to limited genetic variability, genetic diversity and the improved varieties for commercial cultivation, the production is not as much as expected. Therefore, there is a need to develop superior variety of psyllium for high seed and husk yield.

OBJECT OF THE INVENTION

The main object of the invention is therefore, to develop a new distinct early maturing variety with novel indicator/marker distinguishable by visible observation particularly pigment development for detection of the maturity time coupled with high seed and husk. The other object of the invention was to select a new variety with minimum shattering of seeds prior to harvest of the crop thereby increasing the seed and husk yield.

SUMMARY

This invention relates to a new distinct early maturing, high seed and husk yielding variety of psyllium (*Plantago ovata*) designated as variety 'Mayuri' with the distinct pigment marker of the panicles as indicator of the maturity thereby permitting time by harvest and preventing the seed shattering, a problem in *Plantago*. This variety was developed by mutation breeding (gamma rays irradiation). The variety can be propagated asexually, but can conveniently be propagated by seed for commercial cultivation.

BRIEF DESCRIPTION OF THE DRAWINGS

In the drawings accompanying the specification.

DETAILED DESCRIPTION

Figure 1:
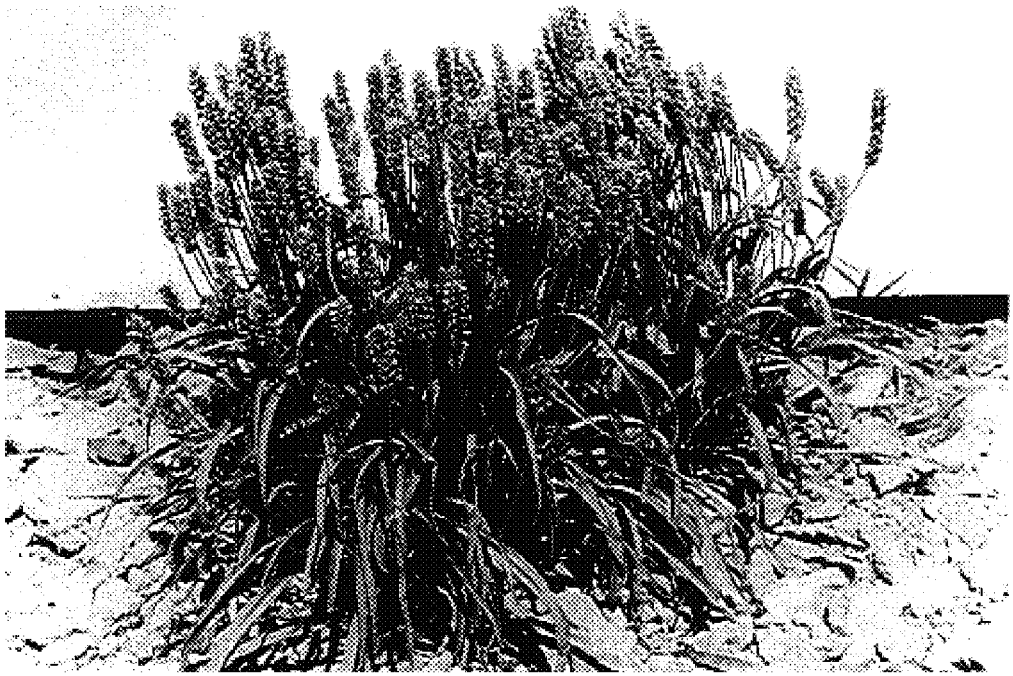
FIG. 1 represents the plant 'Mayuri' in the field.

Under genetic improvement programme of isabgol, mutation breeding (Gamma rays irradiation: 10–100 kR doses) was initiated in an inbred line developed from 'CIMAP/L1' (three generation selfed) to induce variability in its genetic background and select for desirable polygenic mutants (early maturity with indicator/marker for colour at the time of the maturity, high seed and husk yield) suitable for commercial cultivation. Eight promising mutants were selected from different treatments in M2 and evaluated in Initial Evaluation Trial for three consecutive years (1997–1999, M4–M6). These mutants were also evaluated in Bench Scale Trial for three consecutive years (1998–1999), and the most promising mutant CIMAP/S 5 at 20 kR dose was also evaluated further in Pilot Scale Trial for two years (1999–2000).

This work was conducted at main center, Lucknow, Uttar Pradesh, India. On an average, the elite strain CIMAP/S 5 registered its superiority over the control variety Niharika (non-patented) for seed yield per unit area. The elite strain was named as variety 'Mayuri'. 'Mayuri' was asexually produced through stem and rhizome cuttings. Since the plants were multiplied asexually they were highly stable and the progeny resembled the parent. This was further confirmed when the seeds of the asexually grown plants were grown and produced progeny similar to the parent.

TABLE 1 represents the morphological and agronomic characters of the developed variety 'Mayuri' compared to the varieties 'GI 1' and 'Niharika' (non-patented) as control varieties.

| | | Control | |
|---|---|---|---|
| Attributes | New Variety 'MAYURI' | GI 1 | Niharika (non-patented) |
| Plant height (cm) | 40.00 | 43.00 | 45.00 |
| Days to flowering (50%) | 65 (early) | 80 (late) | 72 (medium) |
| Leaves | thin, light green | medium | broad, dark green |
| Growth habit | Semi closed | open | closed |
| No. of panicles/plant | 110 | 85 | 90 |
| Length of spike (cm) | 5.80 | 5.60 | 6.00 |
| Maturity (days) | 100–110 | 130–150 | 120–130 |
| Seed yield (q/ha) | 13.486 | 7.72 | 9.575 |
| Seed husk yield (q/ha) | 3.03 | 1.93 | 2.39 |
| Swelling index | 443.80 | 423.20 | 441.70 |
| Marker/indicator trait (colour of panicle during maturity) | gray purple (distinct) | green (none) | green (none) |

Morphological distinction: A little shorter plant stature, feathery and large number of panicles, thin peduncle, early maturity (100–110 days) and narrow, light green long leaves are the distinct morphological characters of 'Mayuri'.

Taxonomic description of var. 'Mayuri':

1. Genus: *Plantago.*
2. Species: *ovata.*
3. Family: Plantaginaceae.
4. Common name: Isabgol, Psyllium.
5. Leaf: Upper surface: Yellow green group (145A). Lower surface: Yellow green group (145B).
6. Inflorescence colour on maturity: Gray purple group (184D).
7. Inflorescence colour before maturity: Green group (143C).

The color codes are in accordance with The Royal Horticultural Society color chart published by The Royal Horticultural Society, 80 Vincent Square, London SWIP2PE, 1995. The plant 'Mayuri' of Psyllium is an annual herb which attains a height of 30–40 cm. The stem is wholly underground and covered with fine hairs. Tillers arise from the base of the plant. Each tiller bears a rosette of leaves. The leaves are narrowly liner, acuminate, peduncle longer than leaves, arise in the leaf axils and bear ovoid or cylindrical terminal spikes with sessile flowers. The stamens are adnate to the corolla tube and are exerted. The filaments and style are pink. The style usually exceeds the stamens slightly in length and is protogynous. 20–30 cm deep tape roots. The colour of Seeds—dull pinkish (as per the RHC color chart—54D), Boat shaped, outline ovate, length about 1.8–3.3 mm and weight of 100 seeds—0.17 gm.

The variety 'Mayuri' was grown under sub-tropical conditions with an average temperature of 10° C. The morphological data was obtained 80 days after seed was sown. The yield data was obtained at full maturity, 110 days after seed was sown. This variety was developed at main center, Lucknow, Uttar Pradesh, India. No observations were made regarding pest or disease resistance.

When sexually reproduced, the variety was stable. The data presented above indicate that the variety produced no variants of any kind. The trial population was uniform and stable. The trial population reproduced true to type over successive generations for three years. Table 1 presents data indicating that variety 'Mayuri' is superior in several respects to conventional varieties such as 'GI 1' (non-patented) and 'Niharika' (non-patented).

The variety 'Mayuri' has an average plant spread 36 sq cm. The variety's various features are characterized by:

Leaves:
- *Leaf length.*—5.5 cm to 17.0 cm.
- *Phyllotaxy.*—Cluster.
- *Surface texture.*—Chartaceous.
- *Margin type.*—Entire.

Peduncle:
- *Length.*—9.5 to 22.0 cm.
- *Surface texture.*—Smooth.
- *Color.*—141C (Green).

Floret:
- *Length of panicle.*—4.0 cm.

Corolla:
- *Length.*—1.5 mm.
- *Width.*—0.5 mm.
- *Surface texture.*—Chartaceous.
- *Shape.*—Elliptic-obovate.
- *Apex shape.*—Sub obtuse, apiculate.
- *Color.*—69D(pale pink-purple).

Calyx:
- *Length.*—1.0 mm.
- *Width.*—0.2 mm.
- *Surface texture.*—Smooth.
- *Shape.*—Oblong-oblanceolate.
- *Apex shape.*—Acute.
- *Color.*—140B(green), 157C(white).

Filament:
- *Color.*—46A(Red).
- *Length.*—4 mm.

Style:
- *Color.*—46A(Red).
- *Length.*—3 mm.

Pistil number: 1(one).

Stamen number: 4(Four).
Fruit:
*Type.*—Capsule.
*Size.*—3 mm long.
*Colour.*—54D.

The color codes are in accordance with The Royal Horticultural Society Colour Chart published by The Royal Horticultural Society, 80 Vincent Square, London SWIP2PE, 1995.

Yield Trials During Development of 'Mayuri'

Relative performance of 'Mayuri' in different yield evaluation trials is presented in Table 2. The seed lots of the parent inbred line 'CIMAP/L1' were treated with gamma ray in a cobalt ($^{60}$Co) source (10 to 100 kR). These seedlots were sown separately in the farm Lucknow, UP, India and evaluated as indicated in the table 2. The plants generated from the seedlot treated at 20 kR (kilorad) found to be yielding higher in both initial and bench scale trial. So finally the strain 'CIMAP/S-5' was taken to pilot scale trial and found to be high performer compared to the its control 'Niharika' (non-patented). Further, the strain 'CIMAP/S-5' named as 'Mayuri' was observed to be changing the colour of the panicle from green to gray purple indicating the maturity time for harvesting. Also harvesting at this stage minimise the shattering of seeds thereby increasing the yield of the seed and husk. Also the variety 'Mayuri' matured in 100–110 days compared to its control variety 'Niharika' (non-patented) and other strains in different field trials which matures late (130 to 150 days).

RAPD Analysis

The genotype 'Mayuri' is distinct in its RAPD profile in comparison to the control variety 'Niharika' (non-patented). The random primers used for developing the RAPD patterns are as follows:

| Primers | Base sequence |
|---|---|
| MAP 01 | 5' AAA TCG GAG C 3' |
| MAP 02 | 5' GTC XTA CTC G 3' |
| MAP 04 | 5' TGC GCG ATC G 3' |
| MAP 05 | 5' AAC GTA CGC G 3' |
| MAP 06 | 5' GCA CGC CGG A 3' |
| MAP 09 | 5' CGG GAT CCG C 3' |
| MAP 10 | 5' GCG AAT TCC G 3' |
| MAP 11 | 5' CCC TGC AGG C 3' |
| MAP 12 | 5' CCA AGC TTG C 3' |
| MAP 15 | 5' AAG ATA GCG G 3' |
| MAP 16 | 5' GGA TCT GAA C 3' |
| MAP 17 | 5' TTG TCT CAG G 3' |
| MAP 18 | 5' CAT CCC GAA C 3' |
| MAP 19 | 5' GGA CTC CAC G 3' |

(MAP — Medicinal and Aromatic Plants)

Using the above primers, the distinct RAPD profile of the new genotype 'Mayuri' was deduced (FIG. # 2).

The genotype 'Mayuri' or variety 'Mayuri' was developed at Lucknow India under the genetic improvement programme of Lemongrass. The complete RAPD profile for PCR amplified DNA using 14 primers (as mentioned earlier) is available providing evidence of distinctiveness of the genotype 'Mayuri'. Further genotypic pair analysis was utilised for assessing the genetic/molecular distances between Mayuri and control variety 'Niharika'(non-patented) by the help of 60 random primers. Twenty of these primers are designated as MAP primers as designed and synthesised at (Khanuja S P S, Shasany A K, Srivastava A and Kumar S (2000) assessment of genetic relationships in *Mentha* species. *Euphytica.* 111: 121–125). In this analysis the genotypic difference was estimated to be 10.7% between Mayuri and its control variety 'Niharika' (non-patented).

Accordingly the invention in an embodiment provides a new and distinct high yielding, early maturing variety with developmentally expressed pigment marker possessing the following characters:

a. Yellow green group (145A) upper surface, Yellow green group (145B) lower surface of the leaf,
b. inflorescence having green group (143C) florets which turn Gray purple group (184D) on maturity,
c. randomly amplified polymorphic DNA (RAPD) profile for polymerised chain reaction (PCR) amplified DNA segment using 14 primers distinct from the other existing varieties,
d. high seed yield (11 to 12 q/ha) and high seed husk yield (2.3 to 3 kg/ha) compared to other check (control variety),
e. early maturity (100–110) in comparison to other genotypes,
f. development of pigment in the panicle showing stage of colour from green to gray purple as a detectable marker indicating the maturity time for harvesting to avoiding seed shattering.
g. swelling index is 443.80 in comparison to other varieties.

The color codes are in accordance with The Royal Horticultural Society Colour Chart published by The Royal Horticultural Society, 80 Vincent Square, London SWIP2PE, 1995.

Figure 2:
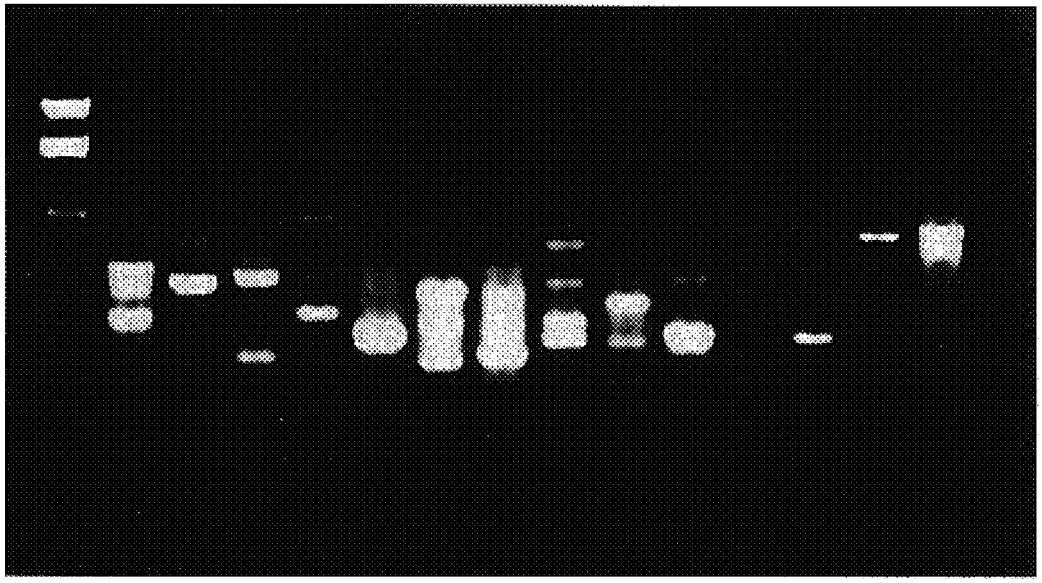
FIG. 2 represents the unique RAPD profile of 'Mayuri'.

FIG. 1 represents the plants 'Mayuri' in the field and FIG. 2 represents the photograph showing the unique RAPD profile of 'Mayuri' wherein Lane 1 represents λ Hind III+EcoRI marker and Lane 2–15 represent profiles with primers MAP 01, MAP 02, MAP 04, MAP 05, MAP 06, MAP 09, MAP 10, MAP 11, MAP 12, MAP 15, MAP 16, MAP 17, MAP 18, MAP 19.

TABLE 2

Mean performance of promising mutants in different yield trials for seed yield in Isabgol

| | Initial Evaluation Trial (g/plot) (RBD, Rep 2, plot size 1.8 Sqm) | | | |
|---|---|---|---|---|
| Entries | 1997 | 1998 | 1999 | Mean |
| 1 CIMAP/S 5 | 322 | 390 | 490 | 401 |
| 2 CIMAP 2337 | 202 | 376 | 340 | 306 |
| 3 CIMAP/S10-1 | 424 | 355 | 450 | 410 |
| 4 CIMAP/S 6 | 494 | 351 | 227 | 357 |
| 5 CIMAP/S 039 | 244 | 312 | 195 | 250 |
| 6 FUR 4-8 | 166 | 286 | 390 | 281 |
| 7 CIMAP 6-9 | 184 | 274 | 278 | 245 |
| 8 BRN 6-5 | 170 | 251 | 292 | 238 |
| 9 GI-1 | 147 | 153 | 150 | 150 |
| 10 NIHARIKA | 170 | 208 | 210 | 196 |
| CD (1%) | 63 | 50 | 55 | — |

TABLE 2-continued

Mean performance of promising mutants in different yield trials for seed yield in Isabgol

| | Entries | Bench Scale Trial (kg/plot) (RBD, Reps 3, plot size 12.96 sqm) 1998 | 1999 | Mean yield |
|---|---|---|---|---|
| 1 | CIMAP/S 5 | 2.265 | 2.575 | 2.420 |
| 2 | CIMAP 2337 | 2.264 | 2.565 | 2.415 |
| 3 | CIMAP/S10-1 | 1.354 | 1.538 | 1.446 |
| 4 | CIMAP/S 6 | 1.552 | 1.527 | 1.540 |
| 5 | CIMAP/S 039 | 1.403 | 1.476 | 1.440 |
| 6 | FUR 4-8 | 1.318 | 1.445 | 1.382 |
| 7 | CIMAP 6-9 | 1.264 | 1.175 | 1.220 |
| 8 | BRN 6-5 | 1.157 | 1.148 | 1.153 |
| 9 | GI-1 | 0.985 | 1.990 | 0.998 |
| 10 | NIHARIKA | 1.333 | 1.335 | 1.134 |
| | CD (1%) | 0.49 | 0.587 | — |

TABLE 2-continued

Mean performance of promising mutants in different yield trials for seed yield in Isabgol

| | Entries | Pilot Scale Trial (mean of two years) (Plot size 67.50 Sqm) seed yield (kg) | seed yield (ql/ha) | seed husk (q/ha) |
|---|---|---|---|---|
| 1 | CIMAP/S 5 | 8.18 | 12.12 | 3.03 |
| 2 | CIMAP 2337 | | | |
| 3 | CIMAP/S10-1 | | | |
| 4 | CIMAP/S 6 | | | |
| 5 | CIMAP/S 039 | | | |
| 6 | FUR 4-8 | | | |
| 7 | CIMAP 6-9 | | | |
| 8 | BRN 6-5 | | | |
| 9 | GI-1 | | | |
| 10 | NIHARIKA | 6.89 | 10.21 | 2.66 |
| | CD (1%) | | | |

SEQUENCE LISTING

```
<160> NUMBER OF SEQ ID NOS: 14

<210> SEQ ID NO 1
<211> LENGTH: 10
<212> TYPE: DNA
<213> ORGANISM: Artificial Sequence
<220> FEATURE:
<223> OTHER INFORMATION: Primers

<400> SEQUENCE: 1

aaatcggagc                                                        10


<210> SEQ ID NO 2
<211> LENGTH: 10
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (4)..(4)
<223> OTHER INFORMATION: n is a, t, g or c

<400> SEQUENCE: 2

gtcntactcg                                                        10


<210> SEQ ID NO 3
<211> LENGTH: 10
<212> TYPE: DNA
<213> ORGANISM: Artificial Sequence
<220> FEATURE:
<223> OTHER INFORMATION: Primers

<400> SEQUENCE: 3
```

-continued tgcgcgatcg 10

<210> SEQ ID NO 4
<211> LENGTH: 10
<212> TYPE: DNA
<213> ORGANISM: Artificial Sequence
<220> FEATURE:
<223> OTHER INFORMATION: Primers

<400> SEQUENCE: 4 aacgtacgcg 10

<210> SEQ ID NO 5
<211> LENGTH: 10
<212> TYPE: DNA
<213> ORGANISM: Artificial Sequence
<220> FEATURE:
<223> OTHER INFORMATION: Primers

<400> SEQUENCE: 5 gcacgccgga 10

<210> SEQ ID NO 6
<211> LENGTH: 9
<212> TYPE: DNA
<213> ORGANISM: Artificial Sequence
<220> FEATURE:
<223> OTHER INFORMATION: Primers

<400> SEQUENCE: 6 cgggatccg 9

<210> SEQ ID NO 7
<211> LENGTH: 9
<212> TYPE: DNA
<213> ORGANISM: Artificial Sequence
<220> FEATURE:
<223> OTHER INFORMATION: Primers

<400> SEQUENCE: 7 gcgaattcc 9

<210> SEQ ID NO 8
<211> LENGTH: 9
<212> TYPE: DNA
<213> ORGANISM: Artificial Sequence
<220> FEATURE:
<223> OTHER INFORMATION: Primers

<400> SEQUENCE: 8 ccctgcagg 9

<210> SEQ ID NO 9
<211> LENGTH: 9
<212> TYPE: DNA
<213> ORGANISM: Artificial Sequence
<220> FEATURE:
<223> OTHER INFORMATION: Primers

<400> SEQUENCE: 9 ccaagcttg 9

<210> SEQ ID NO 10
<211> LENGTH: 10
<212> TYPE: DNA

-continued

```
<213> ORGANISM: Artificial Sequence
<220> FEATURE:
<223> OTHER INFORMATION: Primers

<400> SEQUENCE: 10

aagatagcgg                                                          10


<210> SEQ ID NO 11
<211> LENGTH: 9
<212> TYPE: DNA
<213> ORGANISM: Artificial Sequence
<220> FEATURE:
<223> OTHER INFORMATION: Primers

<400> SEQUENCE: 11

ggatctgaa                                                            9


<210> SEQ ID NO 12
<211> LENGTH: 10
<212> TYPE: DNA
<213> ORGANISM: Artificial Sequence
<220> FEATURE:
<223> OTHER INFORMATION: Primers

<400> SEQUENCE: 12

ttgtctcagg                                                          10


<210> SEQ ID NO 13
<211> LENGTH: 10
<212> TYPE: DNA
<213> ORGANISM: Artificial Sequence
<220> FEATURE:
<223> OTHER INFORMATION: Primers

<400> SEQUENCE: 13

catcccgaac                                                          10


<210> SEQ ID NO 14
<211> LENGTH: 10
<212> TYPE: DNA
<213> ORGANISM: Artificial Sequence
<220> FEATURE:
<223> OTHER INFORMATION: Primers

<400> SEQUENCE: 14

ggactccacg                                                          10
```

We claim:

1. A distinct high yielding, early maturing Psyllium (*Plantago ovata* F.) variety plant 'Mayuri' as described and illustrated with developmentally expressed pigment marker and possessing the following characters:

(a) Yellow green group (145A) upper surface, Yellow green group (145B) lower surface of the leaf, (b) inflorescence having green group (143C) florets which turn Gray purple group (184D) on maturity, (c) randomly amplified polymorphic DNA (RAPD) profile for polymerised chain reaction (PCR) amplified DNA segment using 14 primers distinct from the other existing varieties, (d) high seed yield (11 to 12 q/ha) and high seed husk yield (2.3 to 3 kg/ha) compared to other check (control variety), (e) early maturity (100–110) in comparison to other genotypes, (f) development of pigment in the panicle showing stage of colour from green to gray purple as a detectable marker indicating the maturity time for harvesting to avoiding seed shattering, and (g) swelling index is 443.80 in comparison to other varieties.

* * * * *